United States Patent [19]

Carter

[11] Patent Number: 5,474,531
[45] Date of Patent: * Dec. 12, 1995

[54] APPARATUS AND METHOD FOR ENHANCED INTRAVASCULAR PHONOPHORESIS INCLUDING DISSOLUTION OF INTRAVASCULAR BLOCKAGE AND CONCOMITANT INHIBITION OF RESTENOSIS

[75] Inventor: Robert E. Carter, Arlington, Mass.

[73] Assignee: Coraje, Inc., San Francisco, Calif.

[*] Notice: The portion of the term of this patent subsequent to Nov. 8, 2011, has been disclaimed.

[21] Appl. No.: 332,841

[22] Filed: Nov. 1, 1994

Related U.S. Application Data

[63] Continuation-in-part of Ser. No. 58,222, May 10, 1993, Pat. No. 5,362,309, which is a continuation-in-part of Ser. No. 945,275, Sep. 14, 1992, Pat. No. 5,318,014.

[51] Int. Cl.⁶ .................................................. A61B 17/22
[52] U.S. Cl. ................................................ 604/22; 606/128
[58] Field of Search ............................... 604/22; 606/128, 606/27, 28

[56] References Cited

U.S. PATENT DOCUMENTS

5,058,570  10/1991  Idemoto ............................. 606/128
5,069,664  12/1991  Guess et al. ........................ 604/22
5,362,309  11/1994  Carter ................................ 604/22

Primary Examiner—Ruth S. Smith
Attorney, Agent, or Firm—Walter A. Hackler

[57] ABSTRACT

Ultrasonic apparatus and method for coupling ultrasonic energy into intravascular walls to enhance phonophoresis and for dissolution of intravascular blockages. The apparatus includes a radiator for coupling ultrasonic waves and a piezoelectric crystal, connected with said radiator, for the intravascular generation of ultrasonic waves; said ultrasonic waves being propagated along a longitudinal axis of said piezoelectric crystal. The radiator is sized for intravascular insertion. A transmission cable may be provided for transmitting ultrasonic waves from an ultrasonic transducer to the radiator. A seed liquid is introduced proximate the radiator for promoting cavitation of intravascular fluid. In addition, enhancement of dissolution of intravascular blockages and inhibition of restenosis by chemical agents is significantly increased when combined with ultrasonic energy.

22 Claims, 4 Drawing Sheets

APPARATUS AND METHOD FOR ENHANCED INTRAVASCULAR PHONOPHORESIS INCLUDING DISSOLUTION OF INTRAVASCULAR BLOCKAGE AND CONCOMITANT INHIBITION OF RESTENOSIS

The present application is a continuation-in-part of U.S. patent application Ser. No. 08/058,222, filed May 10, 1993, now U.S. Pat. No. 5,362,309, which is a continuation-in-part of U.S. application Ser. No. 07/945,275, filed Sep. 14, 1992, now U.S. Pat. No. 5,318,014.

BACKGROUND OF THE INVENTION

The present invention is generally related to phonophoresis and is more particularly directed to the intravascular generation of ultrasonic energy for enhanced delivery of drugs and also for the dual purpose of intravascular blockage removal and the prevention of restenosis.

It is known that ultrasound can transport a physiologically active agent, or drug, across a membrane. Phonophoresis is defined as the migration of drug molecules, contained in coupling/contact agents, through the skin under the influence of ultrasound. It has been demonstrated that ultrasound can drive a drug into skeletal muscle and paravertebral nerve, and an increase in percutaneous absorption of several drugs by the influence of ultrasound has been reported by many observers. The usefulness of phonophoresis in chemotherapy is important since the ultrasound localizes drug delivery to a desired area, thus increasing the effectiveness without increasing systemic toxicity.

Ultrasonic energy has been considered for removal of intravascular blockages due to both atherosclerotic plaque and intravascular blood clots. It has been shown that ultrasonic energy is useful in fragmenting plaque and thrombosis, either as a result of mechanical action thereon or cavitation thereof, in which high energy ultrasound applied to liquids generates vapor-filled microbubbles, or "cavities," with the concomitant rapid expansion and collapse of the cavities, accompanied by local intense hydraulic shock leading to fragmentation or dissolution of the thrombosis.

As set forth in U.S. Pat. No. 5,269,291, a miniature ultrasonic ablation tool mounted at the tip of a flexible catheter and deployed in small diameter arteries is useful for removal of intra arterial atherosclerotic plaque and/or blood clots. This reference is incorporated herewith, including all drawings and specification, by this specific reference thereto.

While transluminal coronary angioplasty has gained wide acceptance, acute reocclusion after successful coronary angioplasty occurs in approximately 5% of patients. Late restenosis (generally in less than three months) is a major clinical problem limiting the long-term efficacy of this treatment of atherosclerosis and occurs in 25% to 50% of patients.

The pathogenesis of restenosis is still not entirely clear, but angioscopic observations, autopsy specimens from patients undergoing coronary angioplasty recently, and atherectomy samples from patients with restenosis have demonstrated that the pathophysiologic process leading to acute occlusion after coronary angioplasty are mainly related either to predominantly thrombotic mechanisms or major plaque dissection with intimal flaps and superimposed thrombosis, and that the pathophysiologic events leading to chronic restenosis involved vascular injury, platelet deposition and thrombosis, organization and incorporation of thrombi and subsequent smooth muscle cell proliferation and connective tissue synthesis.

Because excessive platelet deposition at the site of coronary angioplasty and finally smooth muscle cell proliferation appears central to the process of restenosis, the use of an agent directed at the thrombus and smooth muscle cell has been considered. A number of agents have been reported to inhibit smooth muscle cell proliferation, including heparin, immunosuppressants such as cyclosporin, fish oil and omega-3 fatty acid, calcium channel blockers, corticosteroids, baptopril and other inhibitors.

The ultrasonic apparatus of the present invention is specifically useful for the enhanced phonophoresis and the dissolution of intravascular blockages with concomitant treatment for inhibition of restenosis.

SUMMARY OF THE INVENTION

In accordance with the present invention, ultrasonic apparatus generally includes a radiator for coupling ultrasonic waves into intravascular walls and fluids, a piezoelectric crystal connected with the radiator for the generation of ultrasonic waves, and, importantly, a separate lumen for promoting cavitation of the intravascular fluid proximate the radiator. This cavitation is important in the enhancement of phonophoresis.

More specifically, the radiator may be sized for intravascular insertion and the lumen for promoting cavitation may include a seed fluid for introduction into the intravascular fluid proximate the radiator.

The seed fluid may comprise an aqueous saline solution containing carbon dioxide with the carbon dioxide content in the solution being at most about 10 grams per weight per liter of solution. In addition, the seed fluid may include a separate composition having activity for the inhibition of restenosis, such as, for example, heparin. The apparatus of the present invention enhances the delivery of restenosis inhibiting drugs into the vascular wall.

Further, a vessel may be provided for storing the aqueous saline solution at a pressure greater than atmospheric pressure. Also provided is a tube for transferring the pressurized aqueous solution into the lumen from an exterior container.

A valve for controlling the flow of the seed fluid into the lumen provides a means for controlling the rate of clot dissolution.

Additionally, the apparatus may include amplifier means, interconnected between the radiator and the piezoelectric crystal, for transmitting and amplifying mechanical vibration of an ultrasonic frequency from the piezoelectric crystal to the radiator.

More specifically, the amplifier may comprise a cylindrical member having two regions of different cross-sectional area, with a larger cross-sectional region attached to the piezoelectric crystal, and a smaller cross-sectional region attached to the radiator.

In addition, the present invention, in combination, provides an ultrasonic surgical apparatus which includes a catheter having at least one lumen therethrough and adapted for intravascular positioning along with an ultrasonic transducer disposed in the catheter lumen at a distal end thereof. Piezoelectric crystal for generating ultrasonic waves and radiator for coupling ultrasonic waves into clots may be provided, both being sized for intravascular insertion. Also provided is a lumen for promoting cavitation of the intravascular fluid proximate the radiator.

In addition, a power source may be provided and disposed exterior to a proximate end of the catheter and electrically connected to the ultrasonic transducer through the catheter lumen, causing the piezoelectric crystal to generate ultrasonic waves.

Alternatively, ultrasonic waves may be generated from an ultrasonic transducer located outside of the patient. A radiator may be disposed at a distal end of the catheter and sized for intravascular positioning. An amplifier is provided for coupling the ultrasonic transducer to the radiator.

Further specific enhancement of clot dissolution may be obtained through the use of active agents in combination with the ultrasonic transducer.

The active agent may be introduced into the intravascular fluid through a lumen. The lumen may terminate in a cowling circling the radiator tip which extends externally from the catheter. Another embodiment provides for a lumen with a probe tip surrounding an internally disposed radiator. In this embodiment the tip includes at least one outlet aperture therein for directing the agent toward the intravascular wall. Preferably the probe tip includes a plurality of outlet apertures for more complete dispersement of the active agent and for enhancement of cavitation.

A method for dissolving intravascular clots in accordance with the present invention generally includes the steps of introducing ultrasonic waves proximate intravascular blockages and promoting cavitation of intravascular fluid proximate the intravascular blockages. Mechanical violence introduced by the cavitation is thereby effectively utilized to enhance the breakup of blockages such as clots.

More particularly, the step of introducing ultrasonic waves may include the step of inserting a catheter having an ultrasonic transducer on one end thereof into a vessel by positioning the ultrasonic transducer proximate a clot. The step of promoting cavitation includes the introduction of seed fluid into the intravascular fluid proximate the clot with the seed fluid including an aqueous saline solution containing carbon dioxide which preferably is maintained at a pressure greater than about 1 atmosphere before introduction into the intravascular fluid.

Alternatively, the method may comprise inserting a catheter into a vessel and positioning the distal end, including radiator means, proximate a clot. Next the method involves transmitting ultrasonic waves from an exterior ultrasonic transducer located at the proximal end of the catheter through a transmission means extending along the catheter.

In addition, an active agent may be utilized in combination with the ultrasonic transducer and/or means for promoting cavitation to promote clot dissolution without damage to artery walls.

Additionally, means may be provided for directing the active agent toward the intravascular walls. In particular, outlet apertures located within a lumen probe tip may be provided for increasing effective delivery of the agent and for enhancing cavitation.

Further, a combination is provided for enhancing clot dissolution activity of a composition and/or inhibiting restenosis. In view of the present cost of such compositions and possible side effects thereof, this combination is a very important advance in the treatment of intravascular blockages.

BRIEF DESCRIPTION OF THE DRAWINGS

A better understanding of the present invention may be had with the consideration of the following detailed description, taken in conjunction with the accompanying drawings in which.

DETAILED DESCRIPTION

Figure 1:
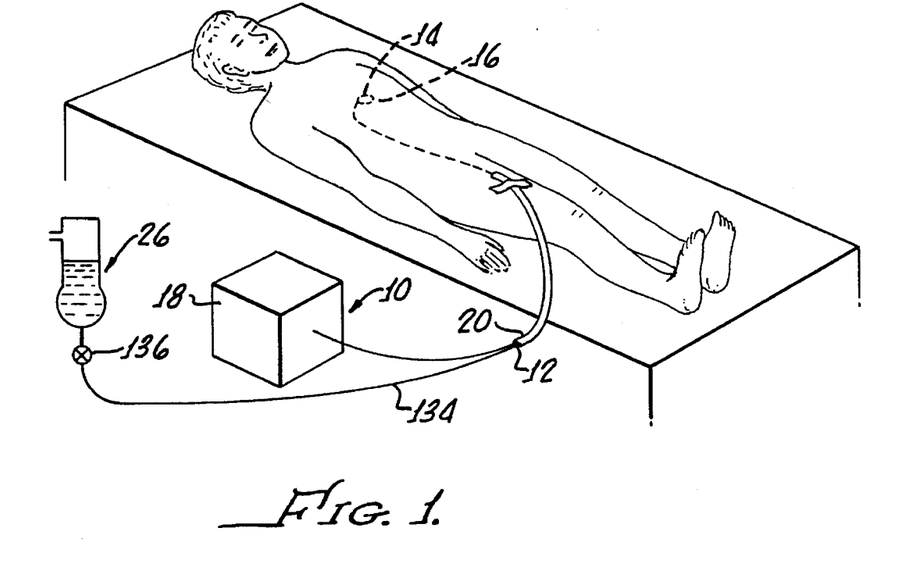
FIG. 1 is a diagram of ultrasonic surgical apparatus in accordance with the present invention for clot ablation, generally showing a catheter, an ultrasonic transducer disposed within a catheter lumen, a power source disposed exterior to a proximate end of the catheter and electrically connected to the ultrasonic transducer through the catheter lumen, and a supply of pressurized seed solution for promoting cavitation in intravascular fluid.

Turning now to FIG. 1, there is shown ultrasonic surgical apparatus 10, generally including a catheter 12, an ultrasonic transducer 14, disposed at a distal end 16 of the catheter 12, and a power source 18 disposed exterior to a proximate end 20 of the catheter 12 and electrically connected to the ultrasonic transducer 14 for causing a piezoelectric crystal 24 (see FIG. 2) to generate ultrasonic waves as hereinafter described in greater detail. It should be appreciated that the catheter 12 and power source 18 may be of any conventional design suitable for use with the ultrasonic transducer 14, with the expected operating frequencies between about 50 kHz and 1.3 MHz, suitable for clot ablation.

Also shown is a storage vessel 26 in fluid communication with the catheter 12 and transducer 14 as will be hereinafter discussed in greater detail.

It is well known in the art that low power ultrasonic resonators (i.e., 20 watt power consumption at resonance under load), such as are used for surgical handpieces, must have all their parts manufactured to very tight tolerances in order to maintain capability of achieving high vibrational motion in air (i.e., unloaded). It is also well known that the addition of an undesigned mass or spring load to the tip significantly reduces the vibration amplitude at resonance, and the power delivery capability. However, it has been found that resonators constructed in accordance with the present invention, i.e., a piezoelectric crystal 24 having an entire end made from active piezoelectric material, and having an inertial node within the body of the ceramic do not need metal pieces with accurate tolerances in order to function. Furthermore, mass, spring, fluid, or point contact-type loads applied to the radiator do not generally cause a loss of amplitude at resonance but instead cause an increased power draw from the AC power supply used to drive the crystal.

Figure 2:
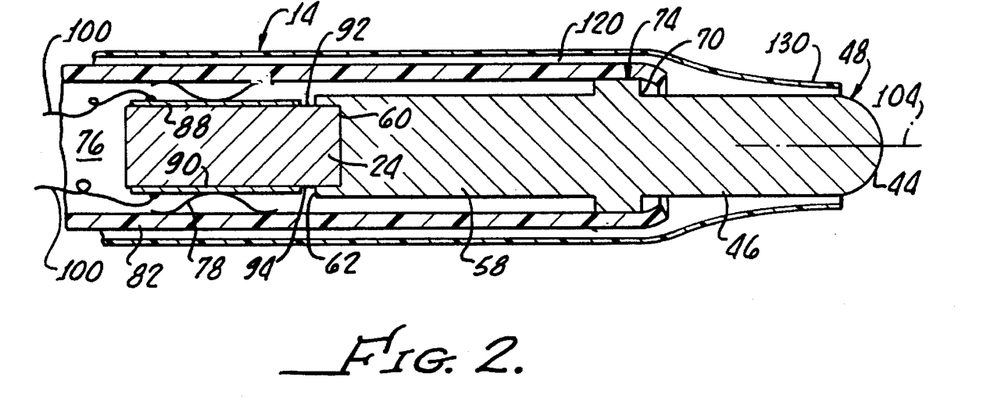
FIG. 2 is an enlarged cross-sectional view of an ultrasonic apparatus in accordance with the present invention.

Turning now to FIG. 2, there is shown an enlarged view of the transducer 14 of the present invention disposed at the distal end 16 of the catheter 12.

A radiator 44 provides means for coupling ultrasonic waves into clots (see FIGS. 3 and 4) which includes a cylindrical body portion 46 and an arcuate radiating surface 48. It should be appreciated that while the radiating surface 48 is shown in the drawing with a generally hemispherical shape, a number of blunt shapes may be utilized as effective radiation of acoustic energy.

As hereinafter described in greater detail, this structure, in part, provides for more efficient radiation of ultrasonic energy in a forward direction than prior art radiators. An amplifier 58 may be interconnected between the piezoelectric crystal 24 and the radiator 44 for transmitting and amplifying mechanical vibration of an ultrasonic frequency from the piezoelectric crystal 24 to the radiator 44.

The radiator 44 and the amplifier 58 may be formed from a single piece of material, such as titanium. Titanium is a preferred material due to its lightweight nature and ability to vibrate longitudinally. Titanium is further known to be relatively non-lossy to sound waves. In addition, it is chemically inert and its hardness resists cavitation erosion. These characteristics make it preferable as a material for the radiator 44.

An opening 60 may be formed in the back face 62 of the amplifier 58 for accepting the piezoelectric crystal 24, which typically would be square in cross-section.

Extending outwardly from a junction 70 of the body portion 46 of the radiator 44 and the amplifier 58 is a circular flange having an "L" portion 74 thereon, which provides means for centering the transducer 14 at the catheter distal end 16 within the catheter lumen 76 with the body portion 46 and radiating surface 48 extending outwardly therefrom.

In addition, a compliant support 78 may be provided adjacent to and surrounding the piezoelectric crystal 24 for supporting and centering the piezoelectric crystal within the catheter lumen 76. The support 78 may be formed of any suitable material which would adhere to an inside wall 80 of the catheter, or the catheter wall 82 may be formed with a berm 78 to accomplish the purpose of supporting the piezoelectric crystal 24 in a centered coaxial relationship within the catheter lumen 76.

Electrodes 88 and 90 may be disposed on opposite sides 92, 94 and interconnected by way of electrical leads 100 to the power source 18 as shown in FIG. 1. The electrodes 88 and 90, as well as the power source 18, may be of conventional design suitable for applying a voltage between the crystal faces 92, 94 in order to cause the mechanical generation of ultrasonic waves, the latter being propagated along a longitudinal axis 104 of the piezoelectric crystal 24.

The piezoelectric crystal 24 may be of any suitable material well known in the art having piezoelectric characteristics such as lead zirconate titanate (PZT). Preferably the cross-section of the piezoelectric crystal 24 is square with a diagonal dimension of about 1 mm to about 6 mm, and for operating in a range of about 50 KHz to about 1.3 MHz, the length, l, of the piezoelectric crystal 24 would be about 1.25 mm to about 12.5 mm in order to sustain power output from the piezoelectric crystal 24 sufficient to cause cavitation for disruption and liquefaction of blood clots.

While the dimensions of the radiator 44 and amplifier 58 are empirically determined, in general the amplifier 58 length is greater than the piezoelectric crystal 24 and amplifier 58 diameter is comparable to the cross-sectional dimensions of the piezoelectric crystal 24. The radiator 44 diameter may be approximately equal to the piezoelectric crystal 24 diagonal dimension.

Figure 3:
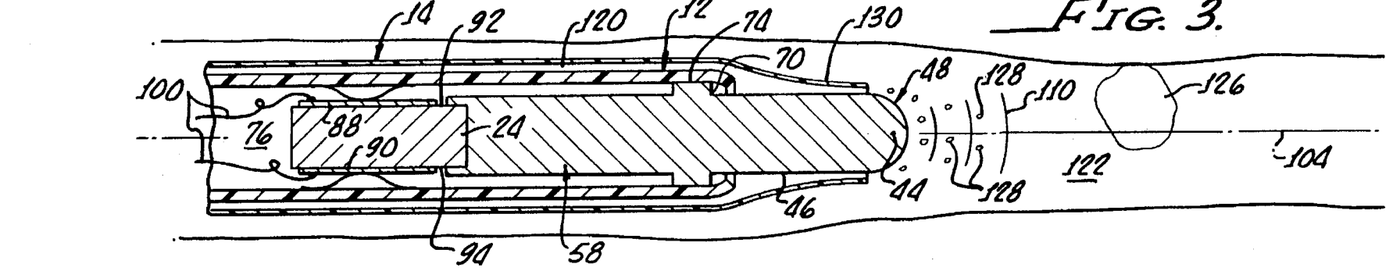
FIGS. 3 and 4 are representations of the use of the apparatus in the present invention in clot dissolution.
Figure 4:
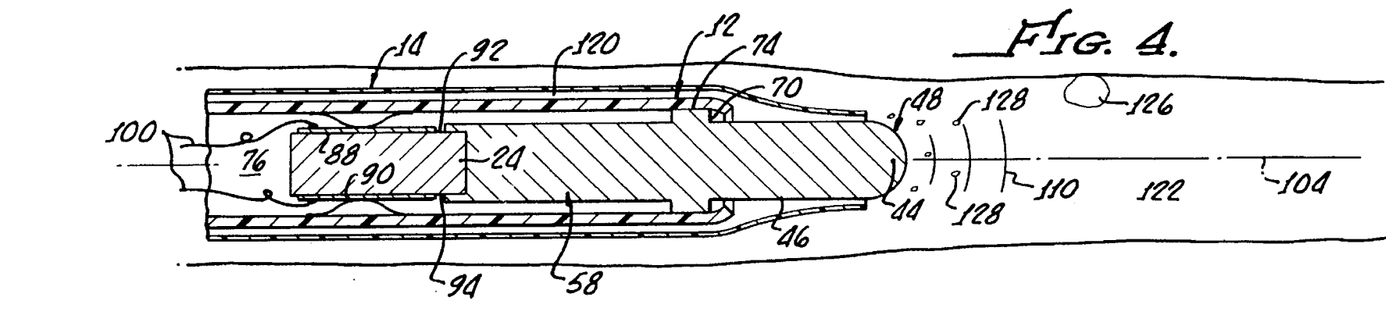

The structure of the transducer 14 in accordance with the present invention promotes the forward projection of acoustic waves 110 along the longitudinal axis 104 as shown in FIGS. 3 and 4.

Referring again to FIG. 2, a lumen 120 in the catheter 12, which surrounds the interior lumen 76, provides a means for both promoting cavitation in intravascular fluid 122, proximate clots 126, and for introducing a composition having clot dissolution activity as will be hereinafter discussed. A representation of the cavitation is illustrated by bubbles 128 within the intravascular fluid 122, and a reduction in clot 126 is represented in FIG. 4.

The lumen 120 terminates in a cowling 130 surrounding the radiator 44 exterior to the catheter 12.

Figure 4A:
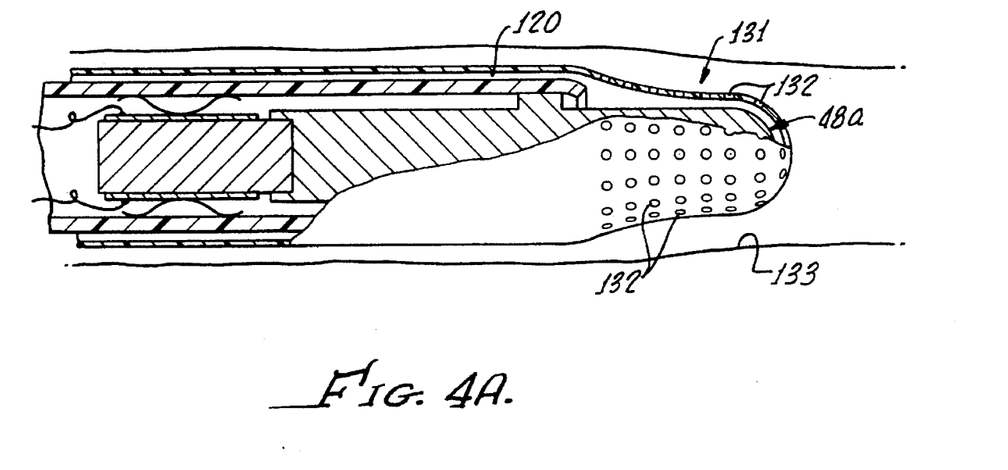
FIG. 4A shows a partially broken-away and cross-sectional view of an alternative embodiment of the present invention which includes a probe tip having a plurality of outlet apertures.

Referring now to FIG. 4A, an alternative embodiment is shown in which the lumen 120 terminates in a probe tip 131. The probe tip 131 may completely surround the radiator surface 48a and may be provided with at least one, but preferably a plurality of, outlet apertures 132 for directing the composition toward the surrounding intravascular walls 133. The composition, preferably a seed fluid as will be hereinafter described, is emitted from the probe tip 131 in a showering fashion. This perforated tip structure effectively delivers the physiologically active composition to the surrounding intravascular walls 133 and fluid. Furthermore, this structure enables cavitation to occur within a large volume of fluid.

Referring again to FIG. 1, a seed liquid at a pressure greater than 1 atm is provided by the storage vessel 26 through a tube 134. A valve 136 provides a means for controlling the rate of clot dissolution through volume regulation of the seed fluid.

Cavitation occurs when the magnitude of the vacuum portion of the pressure-vacuum cycle in an acoustic wave within a liquid medium is sufficiently high that dissolved gases in the fluid come out of solution in the form of small observable bubbles 128. Typically the bubble formation (and/or subsequent collapse during the following pressure cycle) has a characteristic random noise acoustic signature. It is also quite violent mechanically at the bubble site, a property that enhances the efficacy of the transducer 14 in clot dissolution.

The valve 136 is utilized to allow the passage of a small but steady flow of cavitation seed liquid to the intravascular fluid 122.

The seed liquid is an aqueous saline solution impregnated with $CO_2$ (carbon dioxide) in a concentration not exceeding 10 grams weight per liter of fluid. The seed liquid is kept in the vessel 26, sealed against the atmosphere until time of use, when it is carried through a lumen in the catheter to the ablation/dissolution site. As the liquid exits its container, its pressure drops to atmospheric pressure, and the $CO_2$ begins to come out of solution in the form of small gas bubbles (seed bubbles). The concentration of $CO_2$ in the stored solution must be adjusted so that after transit through the lumen, the seed bubble 128 size is still very small (less than 25 microns).

In the presence of the acoustic field of an ultrasonic transducer, the small seed bubbles become sites for cavitation in which they become enlarged, collapse, and/or are forced away from the face of the transducer. The cavitation pressure threshold is lowered considerably, and the density of seed sites is very high—both conditions contributing to the occurrence of cavitation within a large volume of the acoustic medium in front of the transducer. (By contrast, naturally occurring cavitation appears to be confined to a region very close to the face of the transducer.) By adjusting the feed rate of the seed fluid, the resulting cutting/dissolution activity can be controlled for maximum effect. A typical feed rate is 2 cc/min.

Experimental use of the hereinabove described transducer 14, with zero seed fluid flow, has established that when the transducer is held with the force of 60 grams against a submerged cross-sectional sample of totally occluded artery preserved in formaldehyde and the piezoelectric crystal 24 was driven with sufficient voltage at 100 KHz to produce a vibrational amplitude of 6.2 microns (peak) at the radiator 44, steady penetration of the radiator 44 into the clot was observed. The resulting cavity was a smooth-walled imprint of the radiator 44.

With regard to the dissolution of blood clots, a sample of approximately 1 cubic centimeter in volume was removed from a large clot mass and submerged in a transparent plastic tray approximately 1 inch in diameter and ¼ inch deep. The radiator 44 was placed in a permanent position at a depth of about ⅛ inch in the center of the clot and energized as hereinabove described. A portion of the clot within a ¼ inch radius of the radiator 44 was dissolved in two to three seconds.

Continued driving of the piezoelectric crystal 24 produced violent fluid motion and within one minute, the clot had separated into several pieces with each being propelled in eddied currents around the tray and aiming of the transducer at each piece resulted in complete dissolution within one additional minute. After a total lapsed time of about two to three minutes, the appearance of the fluid in the tray was indistinguishable with that of blood. In this experiment, the peak amplitude for clot dissolution was about 5 microns at 100 KHz; thus the voltage requirement is less for clot ablation.

These results are enhanced with seed liquid flow. In addition, it has been observed that bubbles 128 of a certain size (25 to 50 microns) are entrained in the acoustic field of the transducer and projected with very high speed -(not yet measured, but much faster than the eye can follow, perhaps 10 to 15 m/sec) through the intravascular fluid 122. Ultrasound propelled bubbles are postulated to produce sufficient shear forces along their path to separate red blood cells.

It is also expected that the transducer 14 will also exhibit dissolution activity at a distance from the working tip rather than strictly by direct contact as has been the case for intravascular fluid 122 transducers without cavitation enhancement.

It has been further found that the present invention exhibits a synergy with known compositions having clot dissolution activity. That is, the use of ultrasonic energy with a composition having clot dissolution activity increases the dissolution rate up to two orders of magnitude over the use of the composition alone. This is shown in the following example.

EXAMPLE

Two clot samples were prepared as follows:
Cored at 3 mm diameter from clot sample.
Washed in tap water, room temperature.
Weighed, placed at bottom of 1 ml vial with a 5 mm ID.
Covered with 1 ml streptokinase solution (strength: 2,500 units/ml, normal saline diluent).
Immediately following sample immersion, transducer OG-2 (3 mm×3 mm cross section, 120 KHz operating frequency) was moved into contact with one of the clots. The transducer was then operated at a drive level of 75 v peak with 50% duty cycle for a period of 90 seconds.

Temperature of the treated solution after ultrasound exposure was 40° C.

Results were as follows:

| Sample | Initial Weight | Final Weight | Appearance |
|---|---|---|---|
| CONTROL | .142 gm | .109 gm | Core sample intact |
| U.S. + Strep | .120 | .022 | 3 small pieces |

The Example demonstrates the significant effect provided by the combination of ultrasonic energy and composition having clot dissolution activity in actual clot dissolution. This synergism significantly reduces the amount of composition necessary to effect clot dissolution. It can be easily appreciated that any side effects or unwanted activity of the compositions are consequently reduced because of the lower doses necessary to effect clot dissolution when used in combination with ultrasonic energy.

The cavitation created by the apparatus 10 in accordance with the present invention is also useful in the enhancement of phonophoresis and is therefore useful in combination with any known drug, or active agent, and in treatment of conditions by phonophoresis. Such drugs include, but are not limited to:

| | |
|---|---|
| Dexamethasone | Sodium chloride |
| Arabinosyl cytosine | Calcium chloride |
| BCNU | Hydrocortisone |
| Cyclophosphamide's active metabolite | Tetracycline |
| | Streptomycin |
| Nitrogen mustard | Fluorafur |
| Melphalan | Physostigmine |
| Mannitol | Penicillin |
| Zinc oxide and tannic acid | Thiodine |
| Urea and dimethyl sulfoxide | Papain |
| Lignocaine/lidocaine | Interferon |
| Lignocaine and dexamethasone | Penicillin |
| Benzydamine | Streptomycin |
| Fluocinolone acetonide | Tetracycline |
| Ibuprofen | Thiamin and |
| Benzoic acid | Ascorbic Acid |
| Potassium chloride | |

Similar effects are expected with the use of drugs having activity to reduce restenosis. That is, the activity of a drug in reducing restenosis is increased with ultrasonic energy by enhancement of delivery into a vascular wall.

The use of heparin to prevent acute occlusion and chronic restenosis is attractive because of its known antithrombotic effect and inhibitory effect on smooth muscle cell proliferation. Many mechanisms have been described for heparin growth inhibition. The earliest mechanism proposed that heparin, which is negatively charged, "scavenged" cationic growth factors such as fibroblast growth factor and platelet-derived growth factor. It has been shown that smooth muscle cells bind and internalize heparin consistent with receptor-mediated endocytosis.

Unfortunately, doses used for systemic anticoagulant heparinization are accompanied by the potent for hemorrhage, electrolyte shifts, and thrombocytopenia in the acute setting, and osteoporosis and alopecia over longer periods of time. These disadvantages are overcome by the apparatus and method of the present invention utilizing ultrasound to delivery heparin, in which doses may be used which heretofore have been less than conventionally used.

Figure 5:
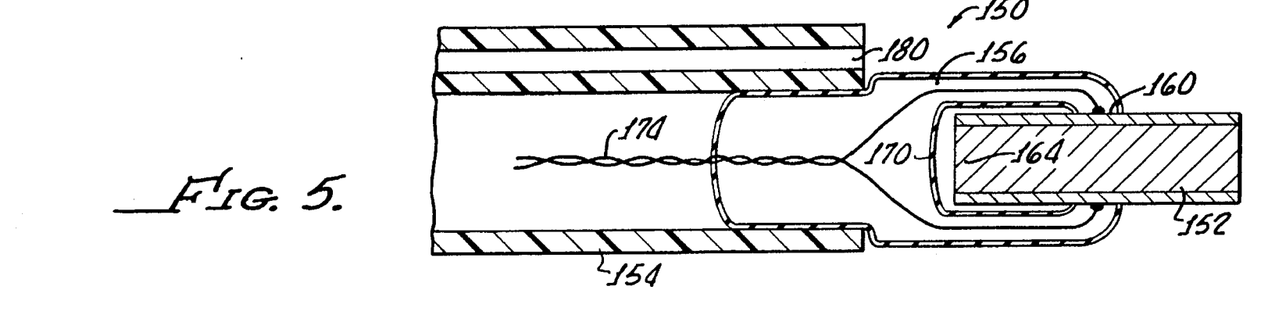
FIG. 5 is a representation of an alternative embodiment of the present invention.

Turning now to FIG. 5, there is shown an alternative embodiment 150 of the present invention, suitable for clot dissolution in combination with a composition having clot dissolution activity as hereinabove described.

This embodiment 150 generally includes a piezoelectric crystal 152 attached to a catheter 154 by means of an elastomeric material 156 which, importantly, is affixed to the crystal 152, only at a midpoint 160 thereof and surrounding a rear end 164 of the crystal 152 without attachment, or adherence thereto, which may leave an air gap 170 between the elastomeric material 156 and the crystal 152.

In this configuration, with the rear end 164 of crystal 152 not being loaded by the elastomeric material, sufficient ultrasonic waves may be introduced into a vessel (not shown in FIG. 5) for the dissolution of clots (not shown in FIG. 5).

As hereinbefore discussed, the piezoelectric crystal 152 may be powered by a set of electrical leads 174 interconnected to the power source 18, shown in FIG. 1. An auxiliary lumen 180 is provided in the catheter 154.to provide means for introducing a composition having clot dissolution activity proximate the crystal 152 within the vessel. The crystal 152 provides a means for intravascular generation of ultrasonic waves within the vessel, in combination with a composition having clot dissolution activity, as hereinabove discussed, and provides a combination for intravascular clot dissolution and apparatus for enhancing clot dissolution activity of a composition.

Figure 6:
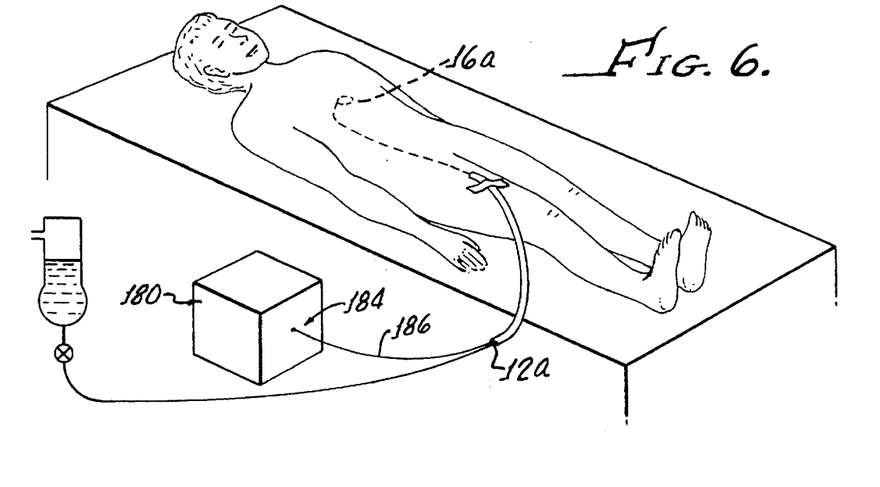
FIG. 6 is a diagram of an alternative embodiment of the present invention in which the ultrasonic transducer is located outside the patient.

FIG. 6 shows another embodiment 178 of the present invention in which the ultrasonic transducer 180 is disposed outside of the patient. Generally, this embodiment includes in combination, a catheter 12a, comprising a distal end 16a sized for intravascular insertion and a proximal end 184 adapted for connection with an ultrasonic transducer 180, and transmission means 186 for coupling the transducer 180 to the distal end 16a of the catheter 12a. Furthermore, and as discussed above in greater detail, separate means are provided for both promoting cavitation of the intravascular fluid proximate the radiator means and for introducing a physiologically active agent into intravascular walls and fluid.

Any suitable ultrasonic transducer device may be utilized in this embodiment. Since the transducer 180 is externally located, and thus is not sized for intravascular insertion, an amplifier means is not necessary if the selected transducer 180, in cooperation with the radiator 44a, is capable of generating sufficient mechanical vibration for clot ablation.

The transmission means 186 may be a wire comprised of any-suitable material well known in the art capable of carrying ultrasonic waves from the transducer 180 to the distal end 16a of the catheter 12a.

Figure 7:
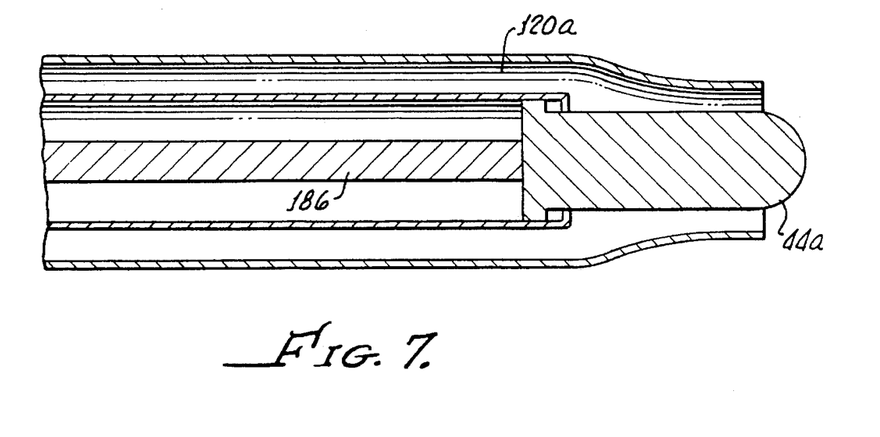
FIG. 7 is an enlargement of a cross-sectional view of the distal end of the catheter shown in FIG. 6.

FIG. 7 shows a cross-sectional view of the distal end 16a of the catheter 12a in accordance with this embodiment. The transmission means 186 preferably extends longitudinally through the catheter 12a and terminates at the distal end 16a wherein a radiator means 44a may be located. As described in detail above, the radiator means 44a functions to direct the ultrasonic energy into selected intravascular walls and fluid.

A catheter lumen 120a which surrounds the transmission means 186 provides means for both promoting cavitation in intravascular fluid proximate the selected intravascular walls and for introducing a physiologically active agent into the intravascular walls and fluid.

As described in detail above, the catheter lumen 120a may end in a cowling, as shown, or the outer lumen may provide at least one outlet aperture therein for directing the agent toward selected intravascular walls. Preferably, a plurality of outlet apertures are provided (as shown in FIG. 4A) for enabling cavitation within a large volume of fluid.

Although there has been hereinabove described a specific arrangement of ultrasonic surgical apparatus and a method for dissolving intravascular blockage and inhibiting restenosis in accordance with the present invention, for the purpose of illustrating the manner in which the invention may be used to advantage, it will be appreciated that the invention is not limited thereto. Accordingly, any and all modifications, variations, or equivalent arrangement which may occur to those skilled in the art should be considered to be within the scope of the invention as defined in the appended claims.

What is claimed is:

1. Ultrasonic apparatus for coupling ultrasound into intravascular walls and fluid comprising:

ultrasonic transducer means for generating ultrasonic waves;

a catheter, comprising a distal end sized for intravascular insertion and a proximal end connected with the ultrasonic transducer;

radiator means, disposed within said distal end of the catheter, for directing the ultrasonic waves into intravascular walls and fluid;

transmission means, extending longitudinally through the catheter, for coupling said ultrasonic transducer to said radiator means;

separate means for both promoting cavitation of the intravascular fluid proximate the radiator means and for introducing a physiologically active agent into the intravascular walls and fluid.

2. The apparatus according to claim 1 wherein the means for both promoting cavitation and introducing a physiologically active agent comprises lumen means for introducing a seed fluid into the intravascular fluid proximate the radiator means.

3. The apparatus according to claim 2 wherein the lumen means comprises a tip, including at least one outlet aperture therein, for directing said seed fluid toward the intravascular walls.

4. The apparatus according to claim 3 wherein the tip includes a plurality of outlet apertures therein, for directing said seed fluid toward the intravascular walls.

5. The apparatus according to claim 1 wherein the physiologically active agent comprises a composition having clot dissolution activity and a composition having activity for inhibiting restenosis.

6. Ultrasonic apparatus for coupling ultrasound into intravascular walls and fluid comprising:

a catheter, comprising a distal end and a proximal end;

radiator means, disposed within the distal end of the catheter and sized for intravascular insertion, for directing ultrasonic waves into intravascular walls and fluid;

means, connected with said radiator means, for generation of the ultrasonic waves; and separate means for both promoting cavitation of the intravascular fluid proximate the radiator means, and for introducing a physiologically active agent proximate the radiator means, said separate means comprising:

lumen means for introducing a seed fluid into the intravascular fluid, wherein said lumen means comprises a tip, including at least one outlet aperture therein for directing the seed fluid toward the intravascular walls.

7. The apparatus according to claim 6 wherein the tip includes a plurality of outlet apertures therein for directing the seed fluid toward the intravascular walls.

8. The apparatus according to claim 6 wherein the seed fluid comprises an aqueous saline solution containing carbon dioxide and a physiologically active agent.

9. The apparatus according to claim 6 wherein the physiologically active agent comprises a composition having activity for inhibiting restenosis.

10. Ultrasonic apparatus for coupling ultrasound into intravascular walls and fluid comprising:

a catheter, comprising a distal end and a proximal end;

radiator means, disposed within the distal end of the catheter and sized for intravascular insertion, for directing ultrasonic waves into intravascular walls and fluid;

ultrasonic transducer means, disposed exterior to the catheter and connected to the proximal end of the catheter for generating ultrasonic waves;

transmission means, extending longitudinally through the catheter, for coupling the ultrasonic waves from the exterior ultrasonic transducer to the radiator means; and separate means for both promoting cavitation of the intravascular fluid proximate the radiator means, and for introducing a physiologically active agent proximate the radiator means, said separate means comprising:

lumen means for introducing a seed fluid into the intravascular fluid, wherein said lumen means comprises a tip, including at least one outlet aperture therein for directing the seed fluid toward the intravascular walls.

11. A method for coupling ultrasound into intravascular walls and fluid, said method comprising the steps of:

inserting a distal end of a catheter into a vessel having intravascular walls;

generating ultrasonic waves from an ultrasonic transducer disposed exterior to said vessel;

providing means for transmitting the ultrasonic waves to the distal end of the catheter;

providing means for radiating the ultrasonic waves from the distal end of the catheter into a selected intravascular wall;

providing means for promoting cavitation of the intravascular fluid proximate said selected intravascular wall; and introducing, into the intravascular fluid proximate said selected intravascular wall, a composition having physiological activity.

12. The method of claim 11 wherein the step of providing means for promoting cavitation, comprises providing a lumen tip, including at least one outlet aperture therein, for directing the composition toward said selected intravascular wall.

13. The method according to claim 11 wherein the step of promoting cavitation comprises introducing into the intravascular fluid proximate the intravascular wall, a seed fluid.

14. The method according to claim 11 wherein the step of promoting cavitation comprises introducing into the intravascular wall a fluid comprising an aqueous saline solution, containing carbon dioxide.

15. The method according to claim 11 wherein the step of introducing a composition comprises introducing an agent for inhibiting restenosis.

16. The method according to claim 11 wherein the step of introducing a composition comprises introducing an agent for clot dissolution.

17. A method for coupling ultrasound into intravascular walls and fluid, said method comprising the steps of:

inserting a distal end of a catheter into a vessel;

providing an ultrasonic transducer for generating ultrasonic waves;

providing means for coupling the ultrasonic waves to a proximal end of the catheter;

providing means for radiating ultrasonic waves from the distal end of the catheter into fluid and intravascular walls;

providing means for promoting cavitation of the fluid proximate the intravascular walls;

introducing into the intravascular fluid a composition, having physiological activity, proximate the intravascular walls; and providing a lumen tip, including at least one outlet aperture therein for directing the composition toward the intravascular walls.

18. The method of claim 17 wherein the lumen tip includes a plurality of outlet apertures therein.

19. The method according to claim 17 wherein the step of providing means for promoting cavitation comprises introducing a seed fluid into the intravascular fluid proximate the intravascular walls.

20. The method of claim 19 wherein the step of introducing a seed fluid comprises introducing an aqueous saline solution containing carbon dioxide.

21. The method of claim 17 wherein the step of introducing a composition comprises introducing an agent for inhibiting restenosis.

22. The method of claim 17 wherein the step of introducing a composition comprises introducing an agent for clot dissolution.

\* \* \* \* \*